US006017559A

United States Patent [19]

Mulqueen et al.

[11] Patent Number: 6,017,559
[45] Date of Patent: Jan. 25, 2000

[54] PREPARATION OF AQUEOUS EMULSIONS

[75] Inventors: Patrick J. Mulqueen, Abingdon; Steven D. Lubetkin, Wantage; Geoffrey W. Smith, Buckland, all of United Kingdom; Eric S. Paterson, Carmel, Ind.

[73] Assignee: Dow AgroSciences LLC

[21] Appl. No.: 08/960,937

[22] Filed: Oct. 30, 1997

Related U.S. Application Data

[63] Continuation of application No. 08/612,919, filed as application No. PCT/US95/08817, Jul. 13, 1995, abandoned.

[30] Foreign Application Priority Data

Jul. 15, 1994 [GB] United Kingdom ................... 9414318

[51] Int. Cl.$^7$ .................................................. A01N 25/28
[52] U.S. Cl. .......................... 424/451; 424/490; 424/496; 264/4.1; 514/963
[58] Field of Search .............................. 424/59, 60, 451, 424/475, 490, 477, 496, 480, 482; 514/311, 963, 312; 264/4.1

[56] References Cited

U.S. PATENT DOCUMENTS

| 4,677,003 | 6/1987 | Redlich et al. ......................... 427/373 |
| 5,025,004 | 6/1991 | Wu et al. ................................. 514/165 |
| 5,925,464 | 7/1999 | Mulqueen et al. .................. 428/402.2 |

FOREIGN PATENT DOCUMENTS

| 442831 A1 | 8/1991 | European Pat. Off. . |
| 0483416 A1 | 5/1992 | European Pat. Off. . |
| 0546174 A1 | 6/1993 | European Pat. Off. . |
| 2078543 | 1/1982 | United Kingdom . |
| WO-A-8903175 | 4/1989 | WIPO . |

OTHER PUBLICATIONS

Pesticide Science, vol. 29, No. 4, 1990, pp. 451–465, P.J. Mulqueen, et al., "Recent Development in Suspoemulsions".

U.K. Search Report; Oct. 17, 1994.
International Search Report; Nov. 29, 1995.

*Primary Examiner*—Jose' G. Dees
*Assistant Examiner*—Kathryne E. Shelborne
*Attorney, Agent, or Firm*—D. Wendell Osborne; Craig E. Mixan

[57] ABSTRACT

A method of controlling the particle size and particle size distribution of an aqueous emulsion having a non-aqueous disperse phase during the production thereof, in which the production of the emulsion is carried out in the presence of a dispersion of a templating agent, such as a polymer latex, and surfactant Particle size and particle size distribution of the dispersion is controlled by selecting the templating agent and surfactant such as to cause deposition of the disperse phase on particles of the dispersed templating agent, such that the particle size distribution of the templating agent provides a template for the particle size distribution of the final emulsion.

29 Claims, No Drawings

PREPARATION OF AQUEOUS EMULSIONS

CROSS-REFERENCE TO RELATED APPLICATIONS

This is a continuation of application Ser. No. 08/612,919, filed Jul. 12, 1996, now abandoned, which is a 371 of PCT/US95/08817, filed Jul. 13, 1995.

This invention relates to the preparation of aqueous emulsions and in particular to the preparation of such emulsions having predictable particle sizes and/or predictable particle size distribution.

The method is particularly suitable for the production of agricultural compositions, for example pesticidal emulsions and the like, having controlled particle size distribution, although it also finds application in various other situations in which controlled particle size emulsions are required either as an end product, or as an intermediate in the production of other products such as microspheres or the like.

In accordance with the invention, we have discovered that an aqueous emulsion having a non-aqueous disperse phase with a controlled particle size distribution can be produced by employing during the production of the emulsion a material such as a latex or a dispersion of a particulate solid, which has a known particle size and/or particle size distribution, the particles of which will form a template for the particle size and/or particle size distribution of the resulting aqueous emulsion. Such materials are referred to herein as "templating agents".

The templating agents suitable for use in the present invention are any materials which will provide, in the presence of appropriate surfactants, a template for the formation of the desired emulsion. Inorganic fillers and the like may be employed as the templating agent, but it is particularly preferred that the templating agent should be a polymer dispersion, particularly an aqueous latex, since it is a relatively straightforward procedure to produce latex particles in predictable particle sizes, and particle size distributions.

The templating agent may be utilised in the production of the aqueous emulsion of the invention in a number of ways. In a preferred embodiment, an emulsion of the disperse phase component(s) of the final emulsion is prepared, using appropriate surfactants, in the presence of the templating agent. In an alternative embodiment, an emulsion may be prepared of the components intended to constitute the disperse phase of the final emulsion, and this emulsion is then combined with the templating agent, in the presence of an appropriate surfactant.

The templating agent and surfactant are chosen such that deposition of the disperse phase of the emulsion takes place on the particles of the dispersed templating agent. The particle size distribution of the templating agent thus provides a template for the particle size distribution of the resulting emulsion.

By this method, the particle size distribution of the resulting aqueous emulsion can be controlled by appropriate control of the particle size distribution of the templating agent.

It is very difficult by conventional methods to produce emulsions with particle sizes and particle size distributions which are both easily reproducible, and easily controlled. By contrast, many of the templating agents which can be employed in accordance with the present invention can easily be produced in particle size distributions which are easy to control, and in particular which have a narrow particle size distribution, or which have a multimodal (e.g., a bimodal) particle size distribution.

The surprising finding on which the present invention is based is that when the templating agent is employed, the shape of the particle size distribution of the resulting aqueous emulsion reflects very closely the shape of the particle size distribution of the templating agent employed. In particular, when a templating agent having a narrow particle size distribution is employed, the particle size distribution of the emulsion produced is correspondingly narrow.

WO89/03135 discloses methods for preparing stabilized water-diluable pesticide compositions, in which latexes are employed as a stabilizing agent. However, there is no suggestion in this reference that the particle size distribution of the stabilizing latex can provide a template for the particle size distribution of the final emulsion. Neither is there any suggestion of the possibility of producing emulsions which are either substantially monodisperse, or multimodal.

EP-A-0483416 discloses the preparation of aqueous latex compositions loaded with various materials, for example dyes and optical brighteners. Again, there is no suggestion that the particle size distribution of the latex can be used to provide a template for a resulting polymeric emulsion. Likewise, there is no suggestion of the preparation either of monodisperse or of multimodal emulsions.

Accordingly, in a first aspect of the invention, there is provided a method of controlling the particle size and particle size distribution of an aqueous emulsion having a non-aqueous disperse phase, during the production thereof, wherein the production of the emulsion is carried out in the presence of a dispersion of a templating agent and surfactant and wherein the control of particle size and particle size distribution of the emulsion is controlled by selecting the templating agent and surfactant such as to cause deposition of the disperse phase on particles of the dispersed templating agent, such that the particle size distribution of the templating agent provides a template for the particle size distribution of the final emulsion.

The breadth of the particle size distribution of a dispersion may be characterized in a number of ways. For particles with a median particle size of greater than about 0.5 micrometer, the breadth of the particle size distribution is typically characterised by "span", defined as $$\text{span} = \frac{D(90) - D(10)}{D(50)},$$

wherein D(10), D(50) and D(90), represent respectively the particle diameters at the 10%, 50% and 90% points in the volume fraction distribution curve. Such measurements may be carried out using laser diffraction techniques, for example using a Malvern Mastersizer™ instrument.

For particles with a median particle size of less than about 0.5 micrometer, breadth of the particle size distribution is typically characterised by "polydispersity", using photon correlation spectroscopy techniques, for example using a Malvern Zetasizer™ or Malvern Hi-C™ instrument. Polydispersity can be derived from the experimentally determined correlation function which is measured by this technique.

To determine the polydispersity, the measured correlation function Y(t) is fitted to a power series $$Y(t) = A + Bt + Ct^2 + \ldots$$

where t is the delay time, and polydispersity is then defined as $$C/B^2$$

For particle sizes of around 0.5 micrometer, either photon correlation spectroscopy or laser diffraction techniques may be employed (although the results measured by the two techniques may not agree absolutely in every case).

The term "monodisperse" as used herein is intended to mean either a dispersion which fulfils the requirement either that its span (as defined above) has a value of 2 or less, preferably 1 or less, or that it has a polydispersity measured as indicated above) of 0.15 or less, preferably 0.1 or less.

In accordance with the present invention, the templating agent, and thus the resulting aqueous emulsion, is preferably monodisperse as defined above.

Accordingly, in a second aspect of the invention, there is provided a method of producing an aqueous emulsion having a disperse non-aqueous phase with a substantially monodisperse particle size distribution, wherein the production of the emulsion is carried out in the presence of a dispersion of a templating agent and surfactant wherein the templating agent has a substantially monodisperse particle size distribution, and wherein the nature and amount of the surfactant is such as to cause deposition of the disperse phase on particles of the dispersed templating agent, such that the particle size distribution of the templating agent provides a template for the particle size distribution of the resulting emulsion.

In an alternative embodiment, the templating agent may be prepared so as to have a multimodal, for example a bimodal particle size distribution. By this method, it is possible to prepare aqueous emulsions which reflect the same multimodal or bimodal particle size distributions.

Accordingly, in a further aspect of the invention, there is provided a method of producing an aqueous emulsion having a dispersed non-aqueous phase with a multimodal particle size distribution, wherein the production of the emulsion is carried out in the presence of a dispersion of a templating agent and surfactant wherein the templating agent has a multimodal particle size distribution, and wherein the nature and amount of the surfactant is such as to cause deposition of the disperse phase on particles of the dispersed templating agent, such that the particle size distribution of the templating agent provides a template for the particle size distribution of the resulting emulsion.

As will be described in more detail hereinafter, emulsions prepared in accordance with the present invention can be used in the preparation of microcapsules and the like. Although many techniques exist for the production of microcapsules, it is in general difficult to produce microcapsules of small particle size (e.g. less than 5000 nm), which are substantially monodisperse. Accordingly, in a further preferred embodiment of this invention, the templating agent may have an average particle size of 5000 nm or less.

As indicated above, the term "dispersion" as used herein in connection with the compositions of the invention is intended to include within its scope both emulsions of essentially liquid materials, prepared employing the said templating agent and surfactant, and dispersions of solid particles. Such solid dispersions can be obtained, for example, by preparing an emulsion as previously described, and then causing the emulsion particle to solidify by various means.

The nucleating agents suitable for use in the present invention are any materials which will provide, in the presence of appropriate surfactants, a template for the formation of the desired emulsion. Inorganic fillers and the like may be employed as the templating agent, but it is particularly preferred that the templating agent should be a polymer dispersion, particularly an aqueous latex.

The term "latex" as used herein is intended to mean any stable suspension of polymer particles in water. Particular examples are polymer suspensions produced in an aqueous suspension emulsion polymerization process, and post-dispersed suspensions, such polyurethanes and ethyl cellulose dispersions.

Suitable latexes for use as templating agents in accordance with the present invention preferably have a particle size of from 30 to 20,000 nm, more preferably from 100 to 5,000 nm.

Preferred latexes comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, the size of the polymeric particles being in the range of from 30 to 20,000 nm, preferably from 100 to 5,000 nm. Small amounts for example 0 to 10 percent of bifunctional monomers may be employed to crosslink the polymers if desired.

The latex may be present when the initial emulsion is formed, in which case the emulsion droplets will begin to combine with the latex immediately they are formed. Alternatively, an emulsion may first be formed by combination of the eventual disperse phase with the surfactant, in the presence of water, and the emulsion thus formed may thereafter be combined with the latex. It is found that the increase in particle size diameter which occurs is that which might be expected if deposition takes place entirely on the surface of the particles of the templating agent.

Although the applicant does not wish to be bound by any particular theory of preparation of the present invention, it is believed that initially incorporation of the disperse phase into the templating agent does not take place by the mechanism of swelling or imbibition. Thus, the increase in particle size due to deposition of the disperse phase on the templating agent can be readily calculated by reference to the known particle size and size distribution of the templating agent, and the quantity of the disperse phase which is added.

Surprisingly it is found that the volume of disperse phase which can be deposited in this way is very large, in comparison with the overall volume of the templating agent. Typically, the volume ratio of the disperse phase to the templating agent can be as high as 100:1, with volume ratios of 10:1 (resulting in an increase in size by a factor of around 2.2 in the templating agent particles) being rapidly and easily achievable.

The disperse phase may preferably take the form of a solution in an appropriate solvent of the material of which it is desired to form the emulsion. For example, the method of the invention may be used to produce pesticidal emulsions, by forming a solution of a pesticide in appropriate water-immiscible solvent, and subsequently emulsifying the solvent, together with appropriate surfactants, in the presence of the templating agent.

Alternatively, the disperse phase may take the form of a single chemical compound, which is liquid at normal temperatures or is heated to a temperature at which it is molten. A suitable example of the latter is the pesticide chlorpyrifos, which can in accordance with the invention be produced in uniform and small particle size distribution.

When a water-immiscible solvent is employed, the nature of the water-immiscible solvent will vary depending upon the nature of any substances which it is desired to incorporate, and the nature of the templating agent. Specific examples however are the aromatic liquids, particularly alkyl substituted benzenes such as xylene or propyl benzene fractions, and mixed naphthalene and alkyl naphthalene fractions; mineral oils, substituted aromatic organic liquids such as dioctyl phthalate; kerosene, polybutenes; dialkylamides of various fatty acids, particularly the dimethyl amides of fatty acids such as the dimethyl amide of caprylic acid; chlorinated aliphatic and aromatic hydrocarbons such as 1,1,1-trichloroethane and chlorobenzene, esters of glycol derivatives, such as the acetate of the n-butyl, ethyl, or methyl ether of diethyleneglycol, the acetate of the methyl ether of dipropyleneglycol, ketones such as isophorone and trimethylcyclohexanone (dihydorisophorone) and the acetate products such as hexyl-, or heptylacetate, and the solvents derived from vegetable oils such as the fatty acid esters, for example methyl oleate. Preferred organic liquids are xylene, propyl benzene fractions, dihydroisophorone, and methyl oleate.

The solvent may, in accordance with a preferred embodiment of the invention, be a volatile material, for example a volatile hydrocarbon such as propane or butane. By this method, the volatile solvent may be volatilized after deposition, leaving behind controlled amounts of solute. The solute may be, for example, a pesticidal material, and may in one embodiment include a film-forming polymer, such that a polymer shell is formed on volatilization of the volatile solvent.

Alternatively, the disperse phase may include reactive monomers, oligomers, or pre-polymers, to facilitate the production of microcapsules and the like from the dispersed particles.

Emulsions prepared in accordance with the present invention appear to be stable over long periods of time, even at very high internal phase volume fractions. The diameter of the disperse phase particles can easily be determined by simple calculation based on the templating agent particle size and the amount of non-aqueous phase employed.

Emulsions in accordance with the present invention may find application, for example, in the manufacture of fuel emulsions and the like, which burn more uniformly, and with less harmful emissions, if the aerosol droplet size is monodisperse.

The predictable manner in which coating of the templating agent particles takes place makes it possible to deliver accurately very small amounts of active materials, by, for example, employing low concentrations of the active materials in the non-aqueous phase used to produce the emulsion, and subsequently evaporating the solvent used.

Similarly, by using the techniques previously described employing polymerizable monomers and the like, and subsequently polymerizing the monomer, oligomer, or prepolymer, core/shell particles can be produced with wall thicknesses which can be controlled very accurately, simply by calculation of the anticipated deposition thickness of the non-aqueous phase, and a knowledge of the concentration of the monomer employed.

The non-aqueous phase employed in the production of such microcapsules may contain chosen amounts of plasticizer for the wall of the finished capsule, thus enabling control of the release kinetics of the finished microcapsules.

In yet a further embodiment, a material can be included within the non-aqueous phase which can be made to react with the continuous phase, either spontaneously after a period of time, or upon alteration of some appropriate parameter of the continuous phase, for example the pH, ionic strength, or the addition of a further reactant. For example, organic derivatives of silicate, titanates, zirconates, and the like, can be employed in the non-aqueous phase, and subsequently hydrolyzed in situ to produce ceramic precursor particles. In such a case, the templating agent may be a polymer dispersion such as a latex as described above, or may be for example a silica or other inorganic material. The monodispersity of the green ceramic particles produced is able to confer substantial advantages in terms of mechanical properties, on the final fired ceramic material.

In yet a further embodiment, the templating agent may be an insoluble pigment particle (either organic or inorganic), and the non-aqueous phase may contain a film-forming polymer, as described above. The method of the invention may thus be used to prepare coated pigment particles, with accurate control over particle size and particle size distribution. The polymer film assists in providing controlled spacing of the pigment particles when a paint containing the pigment dries. This results in improved appearance to the finished surface. Because the thickness of the film-forming coating on the pigment particles may be determined very accurately, it is possible to choose the thickness of the film coating so as to provide particular optical effects, for example using optical interference to generate special colouring effects. Similarly, highly reflective or non-reflective coatings may readily be produced.

Emulsions produced in accordance with the method of the present invention can themselves be employed as templating agents for further processes in accordance with the present invention. Multi-layer coatings may thereby readily be provided. Incorporation of suitable polymerizable monomers in one or more of such layers can be used to generate multiple polymer shells, each shell having predictable and defined properties. The ability to deposit a controlled thickness of non-aqueous phase in each deposition step gives rise to a number of desirable possibilities, such as the provision of different layers with different Tg values, so as for example to provide excellent adhesion together with good wear properties. Outermost layers can be produced with specific chemical functions to bind to specific surfaces, or to release from such surfaces, or with special optical effects, where successive layers are chosen for their refractive indices, or refractive index increments, to maximize or minimize the reflectivity and scattering power. Hollow cores may be provided to maximize such contrasts.

Alternatively, the properties of the various layers can be chosen so as to have specific rheological effects, in which the elasticity and viscosity of each layer is chosen so as to maximize or minimize the storage and loss components at different frequencies.

By the choice of components having appropriate electrical or mechanical properties, the resulting particles can be made to have novel electro-rheological or magneteo-rheological effects.

As indicated above, the method of the invention is particularly suitable for the preparation of pesticidal (e.g. herbicidal, insecticidal, fungicidal, or miticidal) emulsions.

Pesticidal substances suitable for use in the composition in accordance with the invention include

| | |
|---|---|
| amitraz | chlorfenvinphos |
| azinphos-ethyl | chlorflurazuron |
| azinphos-methyl | chlormephos |
| benzoximate | cycloprothrin |
| bifenthrin | betacyfluthrin |
| binapacryl | cyhalothrin |

-continued

| | |
|---|---|
| bioresmethrin | cambda-cyhalothrin |
| chlorpyrifos | alpha-cypermethrin |
| chlorpyrifos-methyl | beta-cypermethrin |
| cyanophos | cyphenothrin |
| cyfluthrin | demeton-S-methyl |
| cypermethrin | dichlorvos |
| bromophos | disulfoton |
| bromopropylate | edifenphos |
| buacarboxim | empenthrin |
| butoxycarboxin | esfenvalerate |
| chlordimeform | ethoprophos |
| chlorobenzilate | etofenprox |
| chloropropylate | etrimphos |
| chlorophoxim | fenazaquin |
| fenamiphos | fenitrothion |
| fenobucarb | fenthiocarb |
| gamma-HCH | fenpropathrin |
| methidathion | fenthion |
| deltamethrin | fenvalerate |
| dicofol | flucythrinate |
| dioxabenzafos | flufenoxuron |
| dioxacarb | tau-fluvalinate |
| endosulfan | formothion |
| EPN | hexaflumuron |
| ethiofencarb | hydroprene |
| dinobuton | isofenphos |
| tetradifon | isoprocarb |
| tralomethrin | isoxathion |
| N-2,3-dihydro-3-methyl-1,3- | malathion |
| thiozol-2-ylidene-2,4- | mephospholan |
| xylidene | methoprene |
| parathion methyl | methoxychlor |
| phosalone | mevinphos |
| phosfolan | permethrin |
| phosmet | phenothrin |
| promecarb | phenthoate |
| resmethrin | pirimiphos-ethyl |
| temephos | pirimiphos-methyl |
| tetramethrin | profenofos |
| xylylcarb | propaphos |
| acrinathrin | propargite |
| allethrin | propetamphos |
| benfuracarb | pyrachlofos |
| bioallethrin | tefluthrin |
| bioallethrin S | terbufos |
| bioresmethrin | tetrachlorinphos |
| buprofezin | tralomethrin |
| triazophos | tetrachlorinphos |
| pyrachlofos | tralomethin |
| tefluthrin | triazophos |
| terbufos | | the following fungicides:

| | |
|---|---|
| benalaxyl | biteranol |
| bupirimate | cyproconazole |
| carboxin | tetraconazole |
| dodemorph | difenoconazole |
| dodine | dimethomorph |
| fenarimol | diniconazole |
| ditalimfos | ethoxyquin |
| myclobutanil | etridazole |
| nuarimol | fenpropidin |
| oxycarboxin | fluchloralin |
| penconazole | flusilazole |
| prochloraz | imibenconazole |
| tolclofos-methyl | myclobutanil |
| triadimefon | propiconazole |
| triadimenol | pyrifenox |
| azaconazole | tebuconazole |
| epoxyconazole | tridemorph |
| fenpropimorph | triflumizole | the following herbicides:

| | |
|---|---|
| 2,4-D esters | clomazone |
| 2,4-DB esters | clopyralid esters |
| acetochlor | CMPP esters |
| aclonifen | cycloate |
| alachlor | cycloxydim |
| anilophos | desmedipham |
| benfluralin | dichlorprop esters |
| benfuresate | diclofop-methyldiethatyl |
| bensulide | dimethachlor |
| benzoylprop-ethyl | dinitramine |
| bifenox | ethalfluralin |
| bromoxynil esters | ethofumesate |
| bromoxynil | fenobucarb |
| butachlor | fenoxaprop ethyl |
| butamifos | fluazifop |
| butralin | fluazifop-P |
| butylate | fluchloralin |
| carbetamide | flufenoxim |
| chlornitrofen | flumetralin |
| chlorpropham | flumetralin |
| cinmethylin | fluorodifen |
| clethodim | fluoroglycofen ethyl |
| fluoroxypyr esters | pendimethalin |
| flurecol butyl | phenisopham |
| flurochloralin | phenmedipham |
| haloxyfop ethoxyethyl | picloram esters |
| haloxyfop-methyl | pretilachlor |
| ioxynil esters | profluralin |
| isopropalin | propachlor |
| MCPA esters | propanil |
| mecoprop-P esters | propaquizafop |
| metolachlor | pyridate |
| monalide | quizalofop-P |
| napropamide | triclopyr esters |
| nitrofen | tridiphane |
| oxadiazon | trifluralin |
| oxyfluorfen | |

Other pesticides such as the nitrification inhibitor nitrapyrin may also be employed. The compositions of the invention may also incorporate mixtures of two or more pesticides.

The pesticide may also be an organosoluble derivative of a pesticidal compound which is itself poorly organosoluble or insoluble, such as cyhexatin dodecylbenzenesulphonate.

the pesticidal compositions of the invention may also include optional adjuvants such as freezing point depressants preferably in amount of 0 percent to 15 percent, flow aids to prevent caking or aid in the re-dispersion of bottom sediment preferably in amounts of 0 percent to 5 percent, thickening agents preferably in amounts of 0 percent to 3 percent, and defoamers preferably 0 percent to 1 percent, to improve the overall properties under field storage and use conditions.

Similarly, conventional pesticide additives such as adjuvant solvents, surfactants for increasing penetration of the active substances or salts may be incorporated into the compositions to maintain or improve biological efficacy of the composition. These may be incorporated into the oil phase or aqueous phase as appropriate.

In order to form an initial aqueous emulsion having the desired droplet size, it is necessary to employ an emulsifier (i.e. a surfactant). The emulsifier can be incorporated into the continuous (aqueous) phase (in which case the emulsifier preferably has a hydrophile-lipophile balance (HLB) number of 12 or more, usually from 12 to 20). Alternatively, the emulsifier may be incorporated into the disperse phase (in which case it preferably has an HLB number of less than 12).

Surfactants which can be advantageously employed herein as emulsifiers can be readily determined by those skilled in the art and include various nonionic, anionic, cationic, or amphoteric surfactants, or a blend of two or more surfactants may be employed. The surfactant employed for the emulsification of the non-aqueous phase should be compatible with the templating agent, and particularly if the templating agent is a latex, should be compatible with the latex, and with any surfactants which may be present in the latex composition.

Examples of suitable nonionic surfactants include polyalkylene glycol ethers, condensation products of alkyl phenols, aliphatic alcohols, aliphatic amines, or fatty acids with ethylene oxide, propylene oxide or mixtures of ethylene and propylene oxides (for example ethoxylated alkyl phenols or ethoxylated aryl or polyaryl phenols and carboxylic esters, solubilized with a polyol or polyoxyethylene) and polyvinyl alcohol/polyvinylactate copolymers.

Suitable cationic surfactants include quaternary ammonium compounds and fatty amines.

Anionic surfactants include the oil-soluble (e.g. calcium, ammonium) salts of alkyl aryl sulphonic acids, oil soluble salts of sulphated polyglycolethers, salts of the esters of sulphosuccinic acid, or half esters thereof with nonionic surfactants and appropriate salts of phosphated polyglycolethers.

Preferred surfactants are those which form and stabilize oil-in-water emulsions such as ethoxylated alcohols, alkoxylated alkyl phenols, polyalkylene oxide copolymers and polyvinyl alcohol/polyvinylacetate copolymers. The surfactant is employed in an amount sufficient to ensure that the emulsion is easily formed and yet does not cause coagulation of the templating agent. This amount will generally be at least 1 percent and preferably from 2 percent to 15 percent, more preferably from 3 percent to 10 percent, and most preferably about 5 percent by weight of the total composition.

In a further alternative embodiment, the disperse phase may include a polymerizable material, such that after formation of the aqueous emulsion, the polymerizable material may be caused to polymerise, thereby generating microcapsules of a desired particle size distribution.

In a further alternative embodiment, the resulting emulsion particles may be caused to solidify after their formation by initially forming the emulsion at a temperature higher than that of the solidification temperature of the disperse phase, and subsequently cooling the emulsion produced to a temperature below the said solidification temperature.

The invention is illustrated by the following Examples. In the Examples, particle size and particle size distribution were determined using a Malvern Zetasizer or Malvern Mastersizer as appropriate. Data determined using the Mastersizer are given as "volume median diameter" (VMD), with an associated "span" as a measure of particle size distribution. Data determined using the Zetasizer are given as "Z-average mean", with an associated "polydispersity" figure, calculated as described in the instrument handbook.

EXAMPLE 1

An aqueous emulsion of styrene/butadiene copolymer (a latex) (12.5 g dry weight) with a particle size 186 nm and a polydispersity of 0.042 (by Malvern Zetasizer) was employed as a templating agent. The emulsion was mixed with water (39.3 g) and a nonionic surfactant (Trade Mark Atlox 4991— 5 g) to give a total weight of 56.8 g. To this was added under high shear an oil composed of chlorpyrifos (28 g) and xylene (15.2 g). After 10 seconds mixing, the product particle size was evaluated and found to be 276 nm (with a polydispersity of 0.144). The calculated value for the particle size if all the oil phase was deposited around the polymer latex was 286 nm.

EXAMPLE 2

An aqueous emulsion of styrene/butadiene copolymer (a latex) (12 g dry weight) with a particle size 122 nm and a polydispersity of 0.179 (by Malvern Zetasizer) was employed as a templating agent. The emulsion was mixed with water (43 g) and a nonionic surfactant (Atlox 4991—5 g) to give a total weight of 60 g. To this was added under high shear an oil composed of chlorpyrifos (26 g) and xylene (14 g). After 10 seconds mixing, the product particle size was evaluated and found to be 191.7 nm (with a polydispersity of 0.051). The calculated value for the particle size if all the oil phase was deposited around the polymer latex was 191 nm.

EXAMPLE 3

The product of Example 2 above was taken (30 g) and diluted to 60 g with water (25 g) and nonionic surfactant (Atlox 4991— 5 g). To this was added under high shear 40 g of an oil composed of chlorpyrifos (26 g) and xylene (14 g). After 10 seconds mixing, the product particle size was evaluated (by Malvern Zetasizer) and found to be 293 nm, with a polydispersity of 0.042. The calculated value for the particle size if all the oil phase was deposited about the previous oil/polymer composite was 289 nm.

EXAMPLE 4

A polystyrene latex (6 g dry weight) with a particle size of 980 nm, and a span of 0.42 (by Malvern Mastersizer) was mixed with water (20 g) and nonionic surfactant (Atlox 4991—5 g). 25 g aromatic solvent (Trade Mark Solvesso 200) was added and the mixture shaken and allowed to equilibrate. The particle size was measured and found to be 1640 nm, with a span of 0.20. The calculated value for the particle size if all the oil phase was deposited about the latex was 1670 nm.

EXAMPLE 5

A polystyrene latex (7 g dry weight) with a particle size of 2250 nm, and a span of 0.73 (by Malvern Mastersizer) was mixed with water and a mixture of nonionic surfactants (Atlox 4991 1 g and Atlox 4913 2 g) to give a weight of 56 g. To this was added a solution of chlorpyrifos (20 g) in xylene (11 g) in which was dissolved 3 g polymethylene polyphenyl isocyanate (PAPI). The mixture was shaken and allowed to equilibrate until the product looked evenly coated with oil when evaluated microscopically. An interfacial polycondensation was effected by the addition of 1 g diethylenetriamine in 9 g water to yield a microcapsule composition containing 20.0% w/w chlorpyrifos. The particle size was measured and found to be 3700 nm, with a span of 0.75 (by Malvern Mastersizer). The calculated value for the particle size if all the oil phase was deposited about the latex and then condensed to a capsule wall without shrinkage was 3870 nm.

EXAMPLE 6

Example 5 was repeated without the inclusion of PAPI in the non-aqueous phase to produce an emulsion with a particle size, by microscopic examination of about 4000 nm. The addition of dipropyleneglycol monomethylether as a co-solvent for the oil phase to wash it off the surface of the latex resulted in the immediate (within measurement time) appearance of the starting latex with a particle size of about 2000 nm, confirming the ease with which the oil phase can be removed by a suitable co-solvent.

EXAMPLE 7

The particle size of a polystyrene latex was measured by the Zetasizer and the Hi-C instruments. This latex (208 g) was then diluted with water (351 g) and 50 g of an alkoxylated nonylphenyl non-ionic surfactant (Trade Mark Renex 95). To the dispersion was added, with stirring 461 g of a 65% w/w chlorpyrifos solution in xylene, sufficient to produce a formulation containing 300 g/l chlorpyrifos.

In a similar manner, a large quantity (692 g) of a 65% chlorpyrifos solution in xylene, sufficient to produce a 450 g/l chlorpyrifos formulation was added to a second dispersion containing the same latex, surfactant, and water (165 g/50 g/199 g respectively). The particle size and polydispersity were determined by both Zetasizer and Hi-C instruments and a calculated vmd determined by the method of Example 6. The results are shown in Table 1.

TABLE 1

| Sample | Hi-C vmd (nm) | polydispersity | Zetasizer (nm) | Calculated vmd (nm) |
|---|---|---|---|---|
| Example 7 | | | | |
| latex | 141 | 0.06 | 152 | — |
| 300 g/l | 238 | 0.06 | 228 | 237 |
| 450 g/l | 292 | 0.077 | 262 | 283 |
| Example 8 | | | | |
| latex | 224 | 0.176 | 205 | — |
| 420 g/l | 455 | 0.165 | 341 | 455 |

EXAMPLE 8

The particle size of an ethylene/vinyl acetate/vinyl chloride terpolymer latex was measured by the Zetasizer and Hi-C instruments. This latex (140 g) was then diluted with water (200 g) and surfactant (Atlox 4991—50 g) and to the dispersion was added, with stirring, 646 g of a 65% w/w chlorpyrifos solution in xylene, sufficient to produce a formulation containing 420 g/l chlorpyrifos. The particle size, polydispersity and calculated vmd were determined as in Example 7. The results are shown in Table 1.

The particle size, polydispersity, and calculated vmd were determined as in Example 7.

Examples 7 and 8 illustrate that, in general, increase of particle size diameter occurs quantitatively corresponding to a deposition of the oil phase on the exterior of the particles. The low values noted for some of the Zetasizer measurements (particularly in Example 8) can be explained by the fact that some dissolution of the oil phase can take place during measurement with the Zetasizer, since measurement with this instrument typically takes place under higher dilution.

EXAMPLE 9

The chlorpyrifos microcapsule of Example 5 was tested for its biological effectiveness in two glasshouse trials. The comparison formulation, DURSBAN 4, was a commercially available 480 g/l emulsifiable concentrate of chlorpyrifos. Both DURSBAN 4 and the sample of Example 5 were applied to test plants at various rates of application (given in mg chlorpyrifos/liter) and their efficacy against cotton leafworm and aphids was assessed as a $T_o$ (initial kill) and $T_7$ (kill after aging plants for 7 days in a controlled environment). The results are shown in Table 2. In a further trial, the effectiveness of the product of Example 5 against cotton leafworm over a 14 day period was evaluated. The results are also tabulated in Table 2.

Table 2 illustrates the effectiveness of the product of Example 5 against cotton leafworm and aphids where it is at least equivalent to DURSBAN 4 in knockdown ($T_o$ days) and superior to DURSBAN 4 in residuality ($T_7$ days).

A further field comparison of Example 5 and DURSBAN 4 was conducted by spraying field plants with an emulsion of chlorpyrifos containing 20 g of each product per 100 liters of water. The effectiveness of the treatment was evaluated by sampling treated leaves at from 0 to 12 days after application and allowing cotton leafworm larvae to feed on the leaves indicated an improved performance of Example 5 over time compared to DURSBAN 4. The results are shown in Table 3.

TABLE 2

| Formulation | mg/liter | Cotton Leafworm % Mortality | | | Aphids % Mortality | |
|---|---|---|---|---|---|---|
| | | $T_0$ | $T_7$ | $T_{14}$ | $T_0$ | $T_7$ |
| DURSBAN 4 | 5 | 10 | — | — | — | |
| | 10 | 14 | — | — | — | |
| | 12.5 | — | — | — | 51 | |
| | 15 | 56 | — | — | | |
| | 20 | 84 | — | — | — | |
| | 25 | 86 | 19 | — | 67 | 3 |
| | 50 | — | 24 | 24 | 93 | 7 |
| | 75 | — | 27 | 25 | 94 | — |
| | 100 | — | 56 | 52 | 100 | 13 |
| | 125 | — | 66 | 79 | — | — |
| | 150 | | | 77 | — | — |
| | 200 | | | — | — | 21 |
| | 400 | | | — | | 47 |
| Example 5 | 5 | 7 | — | — | — | |
| | 10 | 54 | — | — | — | |
| | 12.5 | — | — | — | 57 | |
| | 15 | 83 | — | — | — | — |
| | 20 | 100 | — | — | — | 23 |
| | 25 | 96 | — | — | 83 | 33 |
| | 50 | — | 80 | 100 | 93 | — |
| | 75 | — | 99 | 100 | 94 | 57 |
| | 100 | — | 99 | 100 | 100 | — |
| | 125 | — | 100 | 100 | — | — |
| | 150 | — | 100 | 99 | — | 80 |
| | 200 | — | — | — | — | 89 |
| | 400 | — | — | — | — | |

TABLE 3

| | \% mortality after X days (after treatment) days | | | | | | | | | |
|---|---|---|---|---|---|---|---|---|---|---|
| | 0 | 1 | 3 | 4 | 5 | 6 | 7 | 8 | 9 | 12 |
| DURSBAN 4 | 100 | 98.5 | 82 | 73.5 | 73.5 | 64.5 | 23 | 37 | 43 | 8.5 |
| Example 5 | 100 | 100 | 100 | 100 | 92 | 91 | 76.5 | 72.5 | 65 | 19.5 |

The product of Example 5, despite being a capsule of about 4000 nm in size showed no tendency to sediment, building a thixotropic structure which broke quickly on shaking without the need for any rheological additive, unlike other capsules of a similar nature but with broad particle size distribution (e.g. span>2.0).

We claim:

1. A method of producing microcapsules which comprises first preparing an aqueous emulsion composition having a continuous aqueous phase and a disperse phase, wherein the disperse phase contains a polymerisable material and wherein the production of the emulsion composition is carried out in the presence of a surfactant and a dispersion of a templating agent, wherein the templating agent is a polymer latex that has a particle size distribution
   a) having a span of 1 or less, or
   b) such that the polydispersity of the templating agent is 0.15 or less as measured by photo correlation spectroscopy, and wherein the templating agent and the surfactant are such that deposition of the disperse phase of the emulsion takes place on particles of the dispersed templating agent such that the particle size distribution of the templating agent provides a template for the particle size distribution of the resulting emulsion composition, and subsequently polymerising the polymerisable material in the disperse phase of the emulsion composition to produce the said microcapsules.

2. A method as claimed in claim 1 wherein the templating agent has a particle size distribution
   a) with a span of 1 or less, or
   b) such that its polydispersity is 0.1 or less as measured by photo correlation spectroscopy.

3. A method as claimed in claim 2, wherein the particle size distribution of the emulsion is multimodal.

4. A method as claimed in claim 3, wherein the templating agent has a bimodal particle size distribution.

5. A method as claimed in claim 1 wherein the average particle size of the aqueous emulsion composition is 5 micrometers of less.

6. A method as claimed in claim 1 wherein the disperse phase contains a volatile solvent, and wherein the method includes the step of volatilizing said solvent after said deposition.

7. A method as claimed in claim 6 wherein the volatile solvent is a hydrocarbon.

8. A method as claimed in claim 1 wherein the disperse phase comprises a pesticide.

9. A method as claimed in claim 1 wherein the disperse phase is caused to solidify after the said deposition.

10. A method as claimed in claim 9, wherein the said solidification is caused by cooling.

11. A method as claimed in claim 1 wherein an emulsion is prepared in the presence of the templating agent to obtain the said emulsion composition.

12. A method as claimed in claim 1 wherein an emulsion is first prepared and is then combined with the templating agent to obtain the said emulsion composition.

13. A method as claimed in claim 1 wherein the templating agent constitutes from 10 to 50% by weight of the disperse phase of the emulsion composition.

14. A method as claimed in claim 8 wherein the pesticide is chlorpyrifos.

15. A method as claimed in claim 8 wherein the pesticide is chlorpyrifos; the average particle size of the aqueous emulsion composition is 5 micrometers or less; the disperse phase optionally contains a volatile solvent and the method optionally includes the step of volatilizing said solvent after said deposition; and the templating agent constitutes from 10 to 50 percent by weight of the disperse phase of the emulsion.

16. Microcapules produced by a method which comprises first preparing an aqueous emulsion composition having a continuous aqueous phase and a disperse phase, wherein the disperse phase contains a polymerisable material and wherein the production of the emulsion composition is carried out in the presence of a surfactant and a dispersion of a templating agent, wherein the templating agent is a polymer latex that has a particle size distribution
   a) having a span of 1 or less, or
   b) such that the polydispersity of the templating agent is 0.15 or less as measured by photo correlation spectroscopy, and wherein the templating agent and the surfactant are such that deposition of the disperse phase of the emulsion takes place on particles of the dispersed templating agent such that the particle size distribution of the templating agent provides a template for the particle size distribution of the resulting emulsion composition, and subsequently polymerising the polymerisable material in the disperse phase of the emulsion composition.

17. Microcapsules as claimed in claim 16 wherein the templating agent has a particle size distribution
   a) with a span of 1 or less, or
   b) such that its polydispersity is 0.1 or less as measured by photo correlation spectroscopy.

18. Microcapsules as claimed in claim 17 wherein the particle size distribution of the emulsion composition is multimodal.

19. Microcapsules as claimed in claim 16 wherein the particle size distribution is bimodal.

20. Microcapsules as claimed in claim 16 wherein the average particle size of the aqueous emulsion composition is 5 micrometers or less.

21. Microcapsules as claimed in claim 16 wherein the disperse phase contains a volatile solvent, and wherein the method includes the step of volatilizing said solvent after said deposition.

22. Microcapsules as claimed in claim 16 wherein the volatile solvent is a hydrocarbon.

23. Microcapsules as claimed in claim 16 wherein the disperse phase is caused to solidify after the said deposition.

24. Microcapsules as claimed in claim 16 wherein an emulsion is prepared in the presence of the templating agent to obtain the emulsion composition.

25. Microcapsules as claimed in claim 16 wherein an emulsion is first prepared and is then combined with the templating agent to obtain the emulsion composition.

26. Microcapsules as claimed in claim 16 wherein the templating agent constitutes from 10 to 50 percent by weight of the disperse phase of the emulsion composition.

27. Microcapsules as claimed in claim 16 wherein the disperse phase comprises a pesticide.

28. Microcapsules as claimed in claim 27 wherein the pesticide is chlorpyrifos.

29. Microcapsules as claimed in claim 27 wherein the pesticide is chlorpyrifos; the average particle size of the aqueous emulsion composition is 5 micrometers or less; the disperse phase optionally contains a volatile solvent and the method optionally includes the step of volatilizing said solvent after said deposition; and the templating agent constitutes from 10 to 50 percent by weight of the disperse phase of the emulsion.

* * * * *